United States Patent [19]
Reuter et al.

[11] Patent Number: 5,986,125
[45] Date of Patent: Nov. 16, 1999

[54] PROCESS FOR THE PRODUCTION OF DIALKYL CARBONATES

[75] Inventors: Erich Reuter, Duesseldorf; Walter Knoerr, Illertissen; Bernhard Gutsche, Hilden, all of Germany

[73] Assignee: Henkel Kommanditgesellschaft auf Aktien, Duesseldorf, Germany

[21] Appl. No.: 09/011,682

[22] PCT Filed: Jun. 4, 1997

[86] PCT No.: PCT/EP97/02891

§ 371 Date: Mar. 4, 1998

§ 102(e) Date: Mar. 4, 1998

[87] PCT Pub. No.: WO97/47583

PCT Pub. Date: Dec. 18, 1997

[30] Foreign Application Priority Data

Jun. 13, 1996 [DE] Germany .................. 196 23 508

[51] Int. Cl.⁶ .................. C07C 68/06; C07C 69/96
[52] U.S. Cl. .................................................. 558/277
[58] Field of Search ............................... 558/277

[56] References Cited

U.S. PATENT DOCUMENTS

| | | | |
|---|---|---|---|
| 3,627,810 | 12/1971 | Chang .................... | 558/277 |
| 4,181,676 | 1/1980 | Buysch et al. ............ | 260/463 |
| 4,307,032 | 12/1981 | Krimm et al. ........... | 260/463 |
| 4,381,407 | 4/1983 | Bremus et al. .......... | 560/263 |
| 5,231,212 | 7/1993 | Buysch et al. .......... | 558/277 |
| 5,359,118 | 10/1994 | Wagner et al. ......... | 558/277 |
| 5,387,374 | 2/1995 | Westfechtel et al. .... | 252/56 S |

FOREIGN PATENT DOCUMENTS

| | | |
|---|---|---|
| 0 000 894 | 3/1979 | European Pat. Off. . |
| 0 001 082 | 3/1979 | European Pat. Off. . |
| 0 001 083 | 3/1979 | European Pat. Off. . |
| 0 033 929 | 8/1981 | European Pat. Off. . |
| 0 530 615 | 3/1993 | European Pat. Off. . |
| 0 569 812 | 11/1993 | European Pat. Off. . |
| 31 46 142 | 6/1983 | Germany . |
| 41 29 316 | 3/1993 | Germany . |
| 2 109 265 | 6/1983 | United Kingdom . |
| WO92/10462 | 6/1992 | WIPO . |

OTHER PUBLICATIONS

Chem. Ing. Techn. 68(4): 441–44 (1996).
Ullmann's Encyclopaedie der Techn. Chemie, 4th Ed. vol. 2: 528–533 (1972).

*Primary Examiner*—Michael G Ambrose
*Attorney, Agent, or Firm*—Ernest G. Szoke; Wayne C. Jaeschke; Daniel S. Ortiz

[57] ABSTRACT

The invention relates to a process for the production of higher dialkyl carbonates corresponding to formula (I):

$$(R^1O)(R^2O)CO \qquad (I)$$

which $R^1$ and $R^2$ may be the same or different and represent a linear or branched, saturated or unsaturated and/or alkoxylated alkyl group, by transesterification of lower dialkyl carbonates with higher alcohols in the presence of a catalyst. The process is characterized in that the transesterification is carried out in a column equipped with packings or internals through which the reactants flow in countercurrent to one another. Predominantly symmetrical dialkyl carbonates are obtained.

21 Claims, No Drawings

PROCESS FOR THE PRODUCTION OF DIALKYL CARBONATES

FIELD OF THE INVENTION

This invention relates to a process for the production of higher dialkyl carbonates by transesterification of lower dialkyl carbonates with higher alcohols in the presence of a catalyst, the educts flowing in countercurrent to one another. According to the invention, the transesterification reaction may be carried out both continuously and on the semi-batch principle.

BACKGROUND OF THE INVENTION

Lower alkyl carbonates may be obtained by the reaction of ethylene and propylene glycol carbonates (glycol carbonates) with alcohols in the presence of catalysts. Although this reaction can take place with high selectivity, the processes used to carry it out have a number of disadvantages. In general, the transesterification reaction is relatively slow under normal pressure, so that it is recommended to apply elevated temperatures, in many cases above the boiling point of the alcohol used, which means carrying out the reaction in pressure vessels (EP 1082, EP 1083). Normally, the reaction only proceeds as far as the equilibrium state of the transesterification reaction. After removal from the pressure vessel, the reaction mixture has to be separated very quickly from the catalyst, for example by flash distillation, to prevent the starting compounds from reforming in a reversal of the formation reaction, for example during removal of the lower boiling alcohol by distillation. During separation from the catalyst by distillation, the glycol carbonate still in equilibrium can decompose into carbon dioxide and polyglycols and is thus lost to the transesterification process with a consequent reduction in yield. All the secondary products mentioned interfere with working up. However, even if this removal of the catalyst is satisfactory, several distillations still have to be carried out. First, separation of high boilers from the low boilers is necessary. However, the purification of ethylene glycol by removal of incompletely reacted ethylene glycol carbonate, which is preferably used for the production of the dialkyl carbonates, is not unconditionally possible because both compounds form an azeotrope. A similar difficulty is encountered when methanol, which is the preferred alcoholic component, has to be separated from the dimethyl carbonate formed. These compounds also form an azeotrope which is difficult to separate by distillation (EP 894). In many cases, higher carbonates are also produced by discontinuous reaction of short-chain carbonates, such as diethyl carbonate, dimethyl carbonate, dibutyl carbonate and/or dipropyl carbonate, with alcohols in a stirred tank reactor. During the reaction, the alcohol formed (methanol, ethanol, propanol, butanol) is distilled off so that the equilibrium position is displaced towards the product side. The product alcohol cannot be distilled off in pure form; a mixture of alcohol and short-chain educt carbonate is always obtained. Where dimethyl carbonate is used, a mixture of azeotropic composition (ca. 30% by weight dimethyl carbonate and 70% by weight methanol) is obtained in the most favorable case. This mixture can only be separated by very elaborate processes, for example azeotropic rectification, or so-called hybrid processes (Chem. Ing. Techn. 68 (1996) No. 4, pages 441–444).

DE 41 29 316 describes a process for the transesterification of glycol carbonates with lower alcohols in which lower alkyl carbonates are obtained. In this process, the formation of an azeotrope is avoided and the reaction takes place under mild conditions.

The problem addressed by the present invention was to provide a simple process for the production of higher dialkyl carbonates. Another problem addressed by the invention was to enable higher dialkyl carbonates with a high percentage content of symmetrical dialkyl carbonates to be produced.

BRIEF SUMMARY OF THE INVENTION

It has surprisingly been found that higher dialkyl carbonates, more particularly symmetrical dialkyl carbonates, can be obtained in high yields and, at the same time, the problem of working up an azeotrope can be avoided by transesterifying lower dialkyl carbonates with higher alcohols, the educts flowing in countercurrent to one another.

DETAILED DESCRIPTION OF THE INVENTION

Accordingly, the present invention relates to a process for the production of dialkyl carbonates corresponding to formula (I):

$$(R^1O)(R^2O)CO \tag{I}$$

in which $R^1$ and $R^2$ may be the same or different and represent a linear or branched, saturated or unsaturated and/or alkoxylated alkyl group containing 6 to 22 carbon atoms, by transesterification of lower dialkyl carbonates with higher alcohols in the presence of a catalyst, the transesterification reaction being carried out in a reaction column equipped with packings or internals and the educts flowing countercurrent to one another.

Dialkyl carbonates

Suitable educts are lower dialkyl carbonates corresponding to formula (I), in which $R^1$ and $R^2$ are preferably the same and represent a hydrocarbon radical containing 1 to 4 carbon atoms, more particularly a linear saturated hydrocarbon radical. Diethyl carbonate or dimethyl carbonate is particularly preferred.

Alcohols

The transesterification of the dialkyl carbonates corresponding to formula (I) is carried out with higher alcohols corresponding to formulas (II):

$$R^1OH \text{ and } R^2OH \tag{II}$$

The higher alcohols (II) may be Guerbet alcohols, fatty alcohols being particularly preferred.

Fatty alcohols

Fatty alcohols in the context of the present invention are primary aliphatic alcohols corresponding to formula (II), in which $R^1$ and $R^2$ are aliphatic, linear or branched hydrocarbon radical containing 6 to 22 carbon atoms and 0 and/or 1, 2 or 3 double bonds.

Typical examples are caproic alcohol, caprylic alcohol, 2-ethylhexyl alcohol, capric alcohol, 2-butyl-1-octanol, lauryl alcohol, isotridecyl alcohol, myristyl alcohol, cetyl alcohol, 2-hexyl-1-decanol, palmitoleyl alcohol, stearyl alcohol, isostearyl alcohol, oleyl alcohol, elaidyl alcohol, petroselinyl alcohol, linolyl alcohol, linolenyl alcohol, 2-octyl-1-dodecanol, elaeostearyl alcohol, arachyl alcohol, gadoleyl alcohol, behenyl alcohol, erucyl alcohol and brassidyl alcohol and the technical mixtures thereof obtained, for example, in the high-pressure or low-pressure hydrogenation of technical methyl esters based on fats and oils or aldehydes from Roelen's oxosynthesis and as monomer fraction in the dimerization of unsaturated fatty alcohols.
Guerbet alcohols Guerbet alcohols are alcohols corresponding to formula (II), in which $R^1$ and $R^2$ are branched alkyl groups containing 12 to 44 and preferably 12 to 22 carbon atoms.

In another embodiment, alkoxylated alcohols may be used, preferably the alcohols mentioned above containing 1 to 20 and preferably 2 to 10 ethylene and/or propylene oxide units per molecule.

According to the invention, 2-ethylhexyl alcohol, 2-butyl-1-octanol, 2-hexyl-1-decanol and 2-octyl-1-dodecanol are particularly preferred alcohol components.
Catalysts According to the invention, any of the usual transesterification catalysts which are mentioned, for example, in DE 41 29 316 may be used. Sodium methanolate and tetraisopropyl titanate, tetra-n-butyl titanate and tetra-2-ethylhexyl titanate are particularly preferred. The catalyst is used in quantities of normally 0.01 to 2.5% by weight and, more particularly, 0.05 to 0.5% by weight, based on the weight of educts.
Processes According to the invention, the transesterification of the dialkyl carbonates may be carried out both continuously and by a semi-batch process. Where quantities below 1,000 t/a are produced, the semi-batch process is preferably used whereas larger quantities are preferably produced continuously.
Continuous process The continuous transesterification of dialkyl carbonates is normally carried out in a reaction column equipped with tower packings and/or internals as described in EP 0 033 929 and DE 31 46 142. The dumped or stacked tower packings to be used are those typically used for distillation which are described, for example, in Ullmann's Encyclopädie der Techn. Chemie. 4th Edition, Vol. 2, pages 528 et seq. or in the technical literature of the equipment manufacturing companies in question. The following are mentioned by way of example: Raschig or Pall rings, Berl-Intalex or Torus saddles, Interpack elements of various materials, such as glass, stoneware, porcelain, carbon, stainless steel, plastics, which may be processed into a mesh-like structure, particularly where metal cloth is used. Dumped and stacked tower packings characterized by a large surface, by thorough wetting and by an adequate residence time of the liquid are preferred. Examples of such packings include Pall and Novolax rings, Berl saddles, BX packings, Montz-Pak, Mellapak, Melladur, Kerapak and CY packings. However, not only packed columns, but also columns with fixed internals are suitable for the process according to the invention. Among the columns with fixed internals, those with bubble trays or valve trays having long residence times and a thorough trasfer of material are preferred. In general, however, other tray columns, for example columns with sieve trays, bubble trays, valve trays, tunnel trays and centrifugal trays, which in turn may be present in various forms, are also suitable. Other typical representatives of suitable reaction columns are described in EP-0 033 929 and in DE-31 46 142.

Reaction columns consisting of two sections, a reaction section with special internals, especially bubble trays, and a pure material transfer section with a stacked transfer packing are particularly preferred.

The column is operated at temperatures of 60 to 250° C. In a preferred embodiment, a solution of the catalyst in the alcohol intended for the transesterification is fed in directly below the transfer packing. The catalyst solution is heated beforehand to the corresponding reaction temperature of 100 to 200° C. and preferably 120 to 180° C. The educt carbonate is fed into the lower part of the column in liquid or gaseous form at a temperature of 150 to 250° C. and preferably at a temperature of 170 to 210° C. The molar quantities used are from 1:2 to 1:4 moles of dialkyl carbonate to the corresponding alcohol. The transesterification takes place in the liquid phase on the column trays and the liquid product carbonate accumulating is discharged at the lower end of the column while the product alcohol formed is removed in gaseous form at the head of the column. Pure product alcohol can be removed at the head of the column whereas the product carbonate accumulates together with the excess educt alcohol and the catalyst at the bottom of the column. The bottom product may be worked up by methods known from the prior art so that the product carbonate is obtained in the required purity. The conversion of the educt carbonate is above 99% so that both the distillate and the bottom product are free from educt carbonate.

In another embodiment, the catalyst is fixedly accommodated in the reaction column and the process is carried out as described above except that there is no addition of catalyst dissolved in the alcohol.
Semi-batch process In the transesterification of dialkyl carbonates by the semi-batch process, the reaction is preferably carried out in a stirred tank reactor surmounted by a column. The column may be of the same type as described for the continuous process. A column consisting of a reaction section, more particularly with bubble trays, and a material transfer section is again preferred. The educt carbonate is introduced into the stirred tank reactor with part of the educt alcohol and the catalyst and is subsequently heated with stirring to a temperature of 150 to 250° C. and preferably to a temperature of 170 to 210° C. A mixture of educt carbonate and product alcohol evaporates into the reaction column into which educt alcohol and catalyst (preheated to the reaction temperature of 80 to 210° C. and, more particularly, 120 to 180° C.) are simultaneously introduced above the reaction zone. The reaction takes place in the same way as in the continuous process. In this case, too, the molar quantities are 1:2 to 1:4 moles of dialkyl carbonate per mole of alcohol. 0 to 100% by weight and preferably 50 to 100% by weight of the quantity of dialkyl carbonate to be reacted and 0 to 90% by weight and preferably 50 to 80% by weight of the quantity of alcohol used may be initially introduced into the stirred tank reactor, the remaining quantities being introduced into the reaction column in the same way as in the continuous process.

In another variant of the process, only educt alcohol and catalyst are initially introduced into the stirred tank reactor, the educt carbonate being introduced into the stirred tank reactor at the same time as the remaining educt alcohol is fed into the column.

EXAMPLES

1. Continuous process

Examples 1 to 7

The reaction of dimethyl carbonate with 2-ethyl hexanol was carried out in a glass reaction column with a diameter of 80 mm. The reaction column consisted of 12 bubble trays in the reaction section and of a structured transfer packing (Sulzer BX) in the material transfer zone. The reaction section was equipped with a jacket heating system and was heated to 120 to 150° C. The dimethyl carbonate was added at the 6th reaction tray while the 2-ethyl hexanol and the sodium methanolate (Examples 1 to 6) or the tetraisopropyl orthotitanate (Example 7) were introduced directly below the material transfer zone. The evaporator used at the bottom of the column was a bubble evaporator with no circulation of the bottom product. The results are set out in Table 1.

TABLE 1

Test results, di-2-ethylhexyl carbonate produced in a continuously operated countercurrent reaction column

| Test | Throughputs g/h | | | Molar ratio | Temperature ° C. | |
|---|---|---|---|---|---|---|
| | DMC | 2EH | Cata.* | 2EH/DMC | Head | Bottom |
| 1 | 269 | 1138 | 7.1 | 2.9 | 64.5 | 178 |
| 2 | 349 | 1066 | 6.7 | 2.1 | 64.5 | 182 |
| 3 | 342 | 1555 | 9.7 | 3.1 | 64.5 | 188 |
| 4 | 249 | 1198 | 7.5 | 3.3 | 64.7 | 180 |
| 5 | 267 | 1155 | 2.9 | 3.0 | 63.5 | 184 |
| 6 | 365 | 1536 | 3.8 | 2.9 | 62.9 | 184 |
| 7 | 267 | 1174 | 7.9 | 3.0 | 63.8 | 183 |

| Test | | Concentration, GC % surface area | | | | | Conversion** % |
|---|---|---|---|---|---|---|---|
| | | MeOH | DMC | 2EH | US | SYM | |
| 1 | Distillate | 99.11 | — | — | — | — | |
| | Bottom product | 1.82 | — | 74.33 | 4.21 | 19.03 | 90.0 |
| 2 | Distillate | 98.9 | 0.25 | — | — | — | |
| | Bottom product | 2.83 | 2 | 47.91 | 13.97 | 33.28 | 78.7 |
| 3 | Distillate | 99.1 | — | — | — | — | |
| | Bottom product | 1.09 | — | 66.3 | 4.88 | 27.27 | 91.8 |
| 4 | Distillate | 99.05 | — | — | — | — | |
| | Bottom product | 0.89 | — | 55.33 | 3.28 | 40.5 | 96.1 |
| 5 | Distillate | 89.31 | 9.89 | — | — | — | |
| | Bottom product | 1.39 | — | 56.71 | 3.28 | 38.53 | 95.9 |
| 6 | Distillate | 90.26 | 8.84 | — | — | — | |
| | Bottom product | 0.62 | — | 55.53 | 3.59 | 40.26 | 95.7 |
| 7 | Distillate | 87.9 | 7.99 | — | — | — | |
| | Bottom product | 1.01 | — | 60.94 | 2.6 | 35.17 | 96.4 |

*Tests 1 to 6 sodium methanolate (30% solution in methanol)
Test 7 tetraisopropyl orthotitanate
**Conversion = [SYM]/([SYM] + [US]* 0.5 + DMC) · 100.

TABLE 1-continued

Test results, di-2-ethylhexyl carbonate produced in a continuously operated countercurrent reaction column Definitions:

| DMC | dimethyl carbonate |
|---|---|
| 2EH | 2-ethyl hexanol |
| Cata. | catalyst |
| MeOH | methanol |
| US | non-symmetrical alkyl carbonate |
| SYM | symmetrical alkyl carbonate |

2. Semi-batch process

Example 8

The reaction was carried out in a 4 liter stirred glass reactor equipped with a double jacket heating system and surmounted by a column. The column consisted of a reaction section with 5 bubble trays and a pure material transfer section with a structured packing (Sulzer DX, height 300 mm). 1,800 g of 2-ethyl hexanol and 10.8 g of sodium methanolate (30% in methanol) were initially introduced into and heated in the reactor. 144 ml per hour of 2-ethyl hexanol were continuously introduced with catalyst above the reaction section of the column. In all, 650 ml of 2-ethyl hexanol were added. At the same time, a total of 560 ml of dimethyl carbonate was introduced into the reactor at a rate of 140 ml per hour. The results are set out in Table 2.

Examples 9 to 14

The reaction was carried out in a 4 liter stirred glass reactor equipped with a double jacket heating system and surmounted by a column. The column consisted of a reaction section with 10 bubble trays (total tray volume 170 ml) and a pure material transfer section with a structured packing (Sulzer DX, height 270 mm). The column diameter was 55 mm. The reaction section of the column was in the form of a double jacket and was heated with thermal oil. 2-Ethyl hexanol and catalyst were initially introduced into the reactor and heated to the reaction temperature. 2-Ethyl hexanol was introduced with catalyst above the reaction section of the column. A constant reflux ratio of 1.0 was adjusted at the head of the column and the methanol formed during the reaction was removed as distillate. The test results are set out in Table 2.

TABLE 2

Test results, di-2-ethylhexyl carbonate produced in a semi-batch stirred reactor surmounted by a column

| | Reaction components | | | Quantities added | | | | Molar ratio 2EH/DMC | Column | Reactor tem- |
|---|---|---|---|---|---|---|---|---|---|---|
| | DMC g | 2EH g | Cata.* g | DMC ml/h | DMC ml | 2EH ml/h | 2EH** ml | moles/ moles | heating ° C. | perature ° C. |
| 8 | 0 | 1800 | 10.8 | 140 | 560 | 144 | 650 | 2.9 | None | 180–220 |
| 9 | 416 | 1800 | 9 | 0 | 0 | 150 | 687.4 | 3.9 | 150 | 190 |
| 10 | 620 | 1800 | 9 | 0 | 0 | 150 | 811.5 | 2.8 | 150 | 192 |
| 11 | 620 | 1800 | 9 | 0 | 0 | 150 | 590 | 2.6 | 150 | 192 |
| 12 | 800 | 1800 | 9 | 0 | 0 | 150 | 685 | 2.0 | 150 | 192 |
| 13 | 620 | 1800 | 9 | 0 | 0 | 150 | 602 | 2.6 | 130 | 192 |
| 14 | 620 | 1800 | 9 | 0 | 0 | 150 | 602 | 2.6 | 100 | 191 |

TABLE 2-continued

Test results, di-2-ethylhexyl carbonate produced in a semi-batch stirred reactor surmounted by a column

| Test | | Concentration, GC % surface area | | | | | Conversion*** % |
|---|---|---|---|---|---|---|---|
| | | MeOH | DMC | 2EH | US | SYM | |
| 8 | Distillate | 98 | 0.3 | 1.7 | — | — | |
| | Reaction prod. | — | — | 40.3 | 1.5 | 58.2 | 98.7 |
| 9 | Distillate | 98.2 | 1.8 | — | — | — | |
| | Reaction prod. | 0.12 | — | 54.6 | 1.7 | 43.4 | 98.1 |
| 10 | Distillate | 98.1 | 1.9 | — | — | — | |
| | Reaction prod. | — | — | 41.7 | 3.0 | 55.1 | 97.4 |
| 11 | Distillate | 98.4 | 1.6 | — | — | — | |
| | Reaction prod. | — | — | 31.3 | 4.2 | 64.4 | 96.8 |
| 12 | Distillate | 95.7 | 4.3 | — | — | — | |
| | Reaction prod. | 0.2 | 0.3 | 19.8 | 12.7 | 66.6 | 90.9 |
| 13 | Distillate | 97.1 | 2.9 | — | — | — | |
| | Reaction prod. | — | — | 39.8 | 4.4 | 55.4 | 96.2 |
| 14 | Distillate | 93.7 | 6.3 | — | — | — | |
| | Reaction prod. | — | — | 42.5 | 3.5 | 53.6 | 96.9 |

*Tests 8 to 14 sodium methanolate (30% solution in methanol)
**The catalyst concentration is 0.1% sodium methanolate
 (30% solution in methanol) based on the 2-ethyl hexanol
***Conversion = [SYM]/([SYM] + [US]* 0.5 + DMC) · 100.

Definitions:

DMC    dimethyl carbonate
2EH    2-ethyl hexanol
Cata.    catalyst
MeOH    methanol
US    non-symmetrical alkyl carbonate
SYM    symmetrical alkyl carbonate

Examples 15 to 16

The tests were carried out in the reactor used for Examples 9 to 14. 2-Butyl-1-octanol was used as the alcohol. The procedure corresponded to that of Examples 8 to 14. The results are set out in Table 3.

TABLE 3

Test results, di-2-butyl-1-octyl carbonate produced in a semi-batch stirred reactor surmounted by a column

| Test | Reaction components | | | Quantities added | | | | Molar ratio 2BO/DMC Moles/moles | Column heating °C. | Reactor temperature °C. |
|---|---|---|---|---|---|---|---|---|---|---|
| | DMC g | 2BO g | Cata.* g | DMC ml/h | DMC ml | 2BO** ml/h | 2BO ml | | | |
| 15 | 550 | 2100 | 10 | 0 | 0 | 150 | 693 | 2.4 | 150 | 192 |
| 16 | 550 | 2100 | 9 | 0 | 0 | 150 | 578 | 2.3 | 150 | 195 |

| Test | | Concentration, GC % surface area | | | | | Conversion*** (%) |
|---|---|---|---|---|---|---|---|
| | | MeOH | DMC | 2BO | US | SYM | |
| 15 | Distillate | 93.5 | 6.5 | — | — | — | |
| | Reaction prod. | 0.6 | — | 42.0 | 9.4 | 48.0 | 91.1 |
| 16 | Distillate | 89.6 | 10.4 | — | — | — | |
| | Reaction prod. | 0.2 | — | 45.3 | 10.4 | 43.7 | 89.4 |

*Tests 15 to 16 sodium methanolate (30% solution in methanol)
**The catalyst concentration is 0.1% sodium methanolate
 (30% solution in methanol) based on the 2-butyl-1-octanol
***Conversion = [SYM]/([SYM] + [US]* 0.5 + DMC) · 100.

Definitions:

DMC    dimethyl carbonate
2BO    2-butyl-1-octanol
Cata.    catalyst

TABLE 3-continued

Test results, di-2-butyl-1-octyl carbonate produced in a semi-batch stirred reactor surmounted by a column MeOH  methanol
US    non-symmetrical alkyl carbonate
SYM   symmetrical alkyl carbonate

We claim:

1. A process for the production of higher dialkyl carbonates of the formula:

$(R^1O)(R^2O)CO$ wherein $R^1$ and $R^2$ may be the same or different and independently represent a member selected from the group consisting of linear or branched alkyl groups containing from 6 to 44 carbon atoms, linear or branched unsaturated aliphatic groups containing from 6 to 22 carbon atoms and linear or branched alkyl groups containing from 6 to 44 carbon atoms and from 1 to 20 alkoxy groups, by transesterification of lower dialkyl carbonates with higher alcohols in the presence of a catalyst which comprises: countercurrently contacting and reacting the lower dialkyl carbonate with the higher alcohol in the presence of the catalyst in a countercurrent flow reaction zone which contains means to promote contact between the lower dialkyl carbonate and the higher alcohol.

2. The process as claimed in claim 1 wherein the transesterification is carried out in a reaction column comprising a lower reaction section with bubble trays and a vertically adjacent material transfer packed section.

3. The process as claimed in claim 2 wherein the lower dialkyl carbonates comprises compounds of the formula $(R^3O)(R^4O)CO$, in which $R^3$ and $R^4$ independently represent a linear saturated alkyl group containing 1 to 4 carbon atoms.

4. The process as claimed in claim 2 wherein the higher alcohols comprise at least one member selected from the group consisting of linear or branched alkyl alcohols containing from 6–44 carbon atoms, linear or branched unsaturated aliphatic alcohols containing from 6 to 22 carbon atoms and linear or branched alkyl groups containing from 6 to 44 carbon atoms and from 1 to 20 alkoxy groups. ?

5. The process as claimed in claim 2, wherein the catalyst comprises at least one member selected from the group consisting of sodium methanolate and tetraisopropyl orthotitanate.

6. The process as claimed in claim 2, wherein the transesterification is carried out at a temperature from of 60° C. to 250° C.

7. The process as claimed in claim 2, wherein 1 to 4 moles of higher alcohol are used per mole of dialkyl carbonate.

8. The process as claimed in claim 2, wherein the process is carried out continuously and the catalyst dissolved in the higher alcohol is introduced into an upper portion of a vertical column reaction zone and the dialkyl carbonate is introduced in gaseous or liquid form into a lower portion of the column below a point at which the catalyst and higher alcohol are introduced into the column.

9. The process as claimed in claim 1 wherein the lower dialkyl carbonates comprises compounds of the formula $(R^3O)(R^4O)CO$, in which $R^3$ and $R^4$ independently represent a linear saturated alkyl group containing 1 to 4 carbon atoms.

10. The process as claimed in claim 9 wherein the higher alcohols comprise at least one member selected from the group consisting of linear or branched alkyl alcohols containing from 6–44 carbon atoms, linear or branched unsaturated aliphatic alcohols containing from 6 to 22 carbon atoms and linear or branched alkyl groups containing from 6 to 44 carbon atoms and from 1 to 20 alkoxy groups.

11. The process as claimed in claim 9, wherein the catalyst comprises at least one member selected from the group consisting of sodium methanolate and tetraisopropyl orthotitanate.

12. The process as claimed in claim 9, wherein the transesterification is carried out at a temperature from of 60° C. to 250° C.

13. The process as claimed in claim 9, wherein 1 to 4 moles of higher alcohol are used per mole of dialkyl carbonate.

14. The process as claimed in claim 9, wherein the transesterification is carried out by a semi-batch process, in an apparatus comprising a reaction column reaction zone surmounting a stirred tank reactor into which 0 to 100% by weight of the dialkyl carbonate is introduced together with 0 to 90% by weight of the higher alcohol to be reacted and the remaining quantity of higher alcohol is introduced into an upper portion of the reaction column.

15. The process as claimed in claim 1, wherein the higher alcohols comprise at least one member selected from the group consisting of linear or branched alkyl alcohols containing from 6–44 carbon atoms, linear or branched unsaturated aliphatic alcohols containing from 6 to 22 carbon atoms and linear or branched alkyl groups containing from 6 to 44 carbon atoms and from 1 to 20 alkoxy groups.

16. The process as claimed in claim 15, wherein the catalyst comprises at least one member selected from the group consisting of sodium methanolate and tetraisopropyl orthotitanate.

17. The process as claimed in claim 1, wherein the catalyst comprises at least one member selected from the group consisting of sodium methanolate and tetraisopropyl orthotitanate.

18. The process as claimed in claim 1, wherein the transesterification is carried out at a temperature from 60° C. to 250° C.

19. The process as claimed in claim 1, wherein 1 to 4 moles of higher alcohol are used per mole of dialkyl carbonate.

20. The process as claimed in claim 1, wherein the process is carried out continuously and the catalyst dissolved in the higher alcohol is introduced into an upper portion of a vertical column reaction zone and the dialkyl carbonate is introduced in gaseous or liquid form a lower portion of the column below a point at which the catalyst and higher alcohol are introduced into the column.

21. The process as claimed in claim 1, wherein the transesterification is carried out by a semi-batch process, in an apparatus comprising a reaction column reaction zone surmounting a stirred tank reactor into which 0 to 100% by weight of the dialkyl carbonate is introduced together with 0 to 90% by weight of the higher alcohol to be reacted and the remaining quantity of higher alcohol is introduced into an upper portion of the reaction column.

* * * * *